United States Patent
Brummel

(10) Patent No.: US 7,432,505 B2
(45) Date of Patent: Oct. 7, 2008

(54) INFRARED-BASED METHOD AND APPARATUS FOR ONLINE DETECTION OF CRACKS IN STEAM TURBINE COMPONENTS

(75) Inventor: Hans-Gerd Brummel, Berlin (DE)

(73) Assignee: Siemens Power Generation, Inc., Orlando, FL (US)

( * ) Notice: Subject to any disclaimer, the term of this patent is extended or adjusted under 35 U.S.C. 154(b) by 335 days.

(21) Appl. No.: 11/418,035

(22) Filed: May 4, 2006

(65) Prior Publication Data
US 2007/0258807 A1 Nov. 8, 2007

(51) Int. Cl.
G01J 5/00 (2006.01)

(52) U.S. Cl. ............. 250/332; 250/339.02; 250/339.14; 250/342; 382/152

(58) Field of Classification Search ............... 250/330, 250/338.4, 339.02, 339.14, 342; 382/152
See application file for complete search history.

(56) References Cited

U.S. PATENT DOCUMENTS

| | | | |
|---|---|---|---|
| 4,227,369 A | 10/1980 | Williams | |
| 4,556,328 A | 12/1985 | Orpet | |
| 4,582,426 A | 4/1986 | Douglas | |
| 4,647,220 A | 3/1987 | Adams et al. | |
| 4,764,025 A | 8/1988 | Jensen | |
| 4,765,752 A | 8/1988 | Beynon et al. | |
| 4,818,118 A | 4/1989 | Bantel et al. | |
| 4,902,139 A | 2/1990 | Adiutori | |
| 5,027,268 A | 6/1991 | Sakurai et al. | |
| 5,111,046 A | 5/1992 | Bantel | |
| 5,180,285 A | 1/1993 | Lau | |
| 5,265,036 A | 11/1993 | Suarez-Gonzalez et al. | |
| 5,272,340 A | 12/1993 | Anbar | |
| 5,287,183 A | 2/1994 | Thomas et al. | |
| 5,294,198 A | 3/1994 | Schlagheck | |
| 5,306,088 A | 4/1994 | Zoerner | |
| 5,319,963 A | 6/1994 | Benford | |
| 5,426,506 A | 6/1995 | Ellingson et al. | |
| 5,447,059 A | 9/1995 | Miller et al. | |
| 5,507,576 A | 4/1996 | Fally | |
| 5,552,711 A | 9/1996 | Deegan et al. | |
| 5,562,998 A | 10/1996 | Strangman | |
| 5,582,485 A | 12/1996 | Lesniak | |

(Continued)

FOREIGN PATENT DOCUMENTS

DE 2250142 10/1972

(Continued)

OTHER PUBLICATIONS

Anonymous; "Infrared Scanner Detects Coating Defects"; Materials Engineering; Oct. 1983; p. 24; vol. 97, No. 10; XP002161401.

*Primary Examiner*—David P. Porta
*Assistant Examiner*—Mark R Gaworecki

(57) ABSTRACT

An online method, system, and computer-readable code for remotely monitoring radiant energy emitted from a turbine blade (106), which may be undergoing an incipient degradation, such as a crack, in a relatively low-temperature, and saturated steam environment of the low pressure stage of a steam turbine. The method and system provide sufficient temporal and spatial resolution to obtain high quality infrared images of the blade areas of interest enabling the system to identify the crack at any of those areas of the blade prior to such a crack growing to a critical length.

5 Claims, 3 Drawing Sheets

U.S. PATENT DOCUMENTS

| | | |
|---|---|---|
| 5,608,845 A | 3/1997 | Ohtsuka et al. |
| 5,625,153 A | 4/1997 | Sawai et al. |
| 5,683,825 A | 11/1997 | Bruce et al. |
| 5,716,720 A | 2/1998 | Murphy |
| 5,748,500 A | 5/1998 | Quentin et al. |
| 5,755,510 A | 5/1998 | Hernandez et al. |
| 5,822,222 A | 10/1998 | Kaplinsky et al. |
| 5,832,421 A | 11/1998 | Santoso et al. |
| 5,838,588 A | 11/1998 | Santoso et al. |
| 5,865,598 A | 2/1999 | Twerdochlib |
| 6,015,630 A | 1/2000 | Padture et al. |
| 6,062,811 A | 5/2000 | Zombo et al. |
| 6,072,568 A | 6/2000 | Pateon et al. |
| 6,109,783 A | 8/2000 | Dobler et al. |
| 6,153,889 A | 11/2000 | Jones |
| 6,285,449 B1 | 9/2001 | Ellingson et al. |
| 6,364,524 B1 | 4/2002 | Markham |
| 6,367,968 B1 | 4/2002 | Ringermacher et al. |
| 6,394,646 B1 | 5/2002 | Ringermacher et al. |
| 6,422,741 B2 | 7/2002 | Murphy et al. |
| 6,422,743 B1 | 7/2002 | Nirmalan et al. |
| 6,437,334 B1 | 8/2002 | Thomas et al. |
| 6,461,035 B2 | 10/2002 | Meinlschmidt et al. |
| 6,480,225 B1 | 11/2002 | Kim |
| 6,690,016 B1 | 2/2004 | Watkins et al. |
| 6,750,454 B2 | 6/2004 | Brown et al. |
| 6,796,709 B2 | 9/2004 | Choi |
| 2001/0005392 A1 | 6/2001 | Schultz et al. |
| 2003/0128736 A1 | 7/2003 | Dailo et al. |
| 2004/0225482 A1* | 11/2004 | Vladimirov et al. ............ 703/2 |
| 2005/0270519 A1* | 12/2005 | Twerdochlib ................ 356/24 |
| 2006/0078193 A1* | 4/2006 | Brummel et al. ............ 382/152 |

FOREIGN PATENT DOCUMENTS

| | | |
|---|---|---|
| DE | 19720461 A1 | 2/1998 |
| EP | 0618432 A2 | 10/1994 |
| EP | 0898158 A2 | 2/1999 |
| GB | 1480347 | 7/1977 |
| GB | 2164147 A | 3/1986 |
| GB | 2313189 A | 11/1997 |
| JP | 61172059 A | 8/1986 |
| JP | 61265569 A | 11/1986 |
| JP | 2003098134 A | 4/2003 |
| WO | WO 9954692 A2 | 10/1999 |

* cited by examiner

INFRARED-BASED METHOD AND APPARATUS FOR ONLINE DETECTION OF CRACKS IN STEAM TURBINE COMPONENTS

FIELD OF THE INVENTION

The invention generally relates to steam turbines, and, more particularly, to infrared-based identifying and monitoring means configured to detect and avoid a crack growing to a critical length in a blade of an operating steam turbine.

BACKGROUND OF THE INVENTION

It is known that a crack, such as incipient cracks that may occur in steam turbine blades, can grow to a critical length and may lead to a point of failure of the blade, which can result in costly damage of the steam turbine. One area that has been susceptible to such occurrences is the last row of blades in the low-pressure section of a multi-section steam turbine. The blades in this last row have a relatively large diameter and the operational environment is a relatively low-temperature (e.g., near room temperature) and foggy environment due to the presence of saturated steam and/or water droplets.

One technique that has attempted to address the foregoing issues relies on detecting vibration abnormalities in an operating steam turbine. In particular, this technique analyzes the vibration characteristics of blades of interest by means of a blade vibration monitor (BVM). This technique is able to indicate high stresses, which could lead to cracks and eventually to a catastrophic failure of the blade, however, this technique is unable to provide a direct and reliable indication as to whether a crack has formed in the blade and how such a crack may be developing. Additional limitations concomitant with this technique may be as follows: The BMV sensing is generally performed either during the commissioning of a new turbine or during the recommissioning after an outage of a field-deployed steam turbine. The interpretation of the BMV signals generally requires service personnel with substantial training. Thus, the use of this technique entails a labor-intensive service for a relatively short period of time rather than a continuous blade monitoring that can run automatically as the turbine operates. It is believed that prior to the present invention those skilled in the art have shied away from the use of infrared sensing techniques to address the foregoing issues in view of the substantial challenges involved in capturing data with enough contrast and resolution for a fast rotating steam turbine component in a relative low-temperature environment and in the presence of saturated steam.

BRIEF DESCRIPTION OF THE DRAWINGS

The above and other advantages of this invention will be more apparent from the following description in view of the drawings in which.

DETAILED DESCRIPTION OF THE INVENTION

Figure 1:
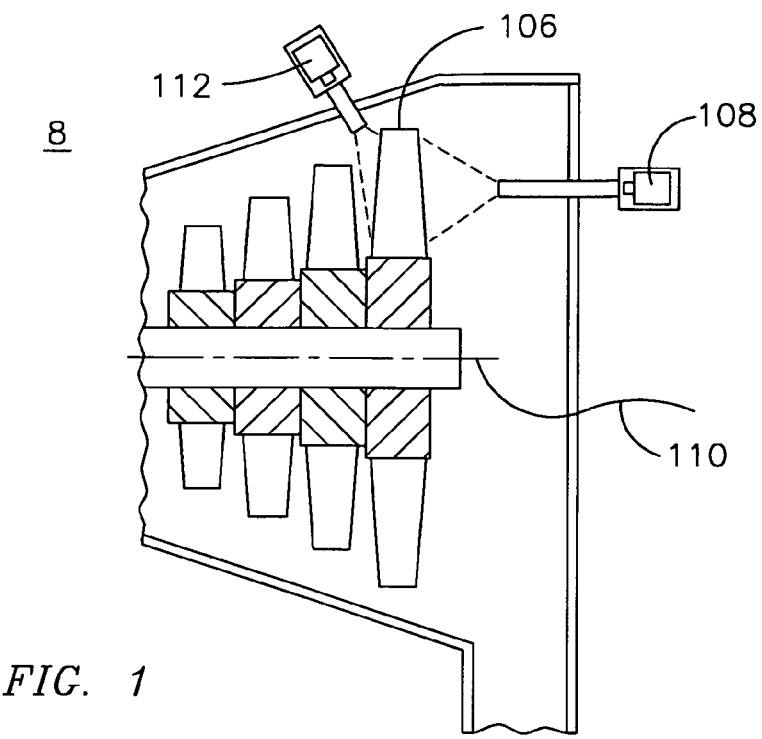
FIG. 1 is a schematic representation of an exemplary online infrared-based monitor as may be used to monitor steam turbine blades.

Aspects of the present invention are directed to sensing potential failure conditions that may occur in rapidly moving steam turbine components, such as may operate in a relatively low-temperature and saturated steam environment, as may be encountered in the last row of blades in a low-pressure stage of a multi-stage steam turbine 8, as exemplarily illustrated in FIG. 1. It will be understood that such a monitoring application should be construed in an illustrative sense and not in a limiting sense since the concepts of the present invention are neither limited to any particular stage of a multi-stage steam turbine nor are such concepts limited to any particular row of blades.

The inventor of the present invention has innovatively recognized a relatively fast infrared sensing system that is able to operate with sufficient resolution, contrast, and speed in a low-temperature (e.g., near room temperature) and saturated steam environment. In one exemplary embodiment, the infrared sensing system may be coupled to an expert system for measuring relative spatial/time radiance. The expert system may use a degradation model to generate advisory information and actively avert a failure of the component. Aspects of the present invention may allow identifying incipient cracks that may form on a blade surface, measure their growth, and forecast and prevent failure of the blade.

In one exemplary embodiment, a system embodying aspects of the present invention may be configured to measure the radiance of a moving turbine blade in a steam turbine under operating conditions. For example, the blades may be moving at supersonic linear speeds in the order of approximately Mach 2. It is believed that the system will monitor, essentially in real-time (such as with a slight time delay of approximately 5-10 seconds as may be required for performing data processing), during turbine operation, the formation and progression of potentially critical defects. As the measuring system can be integrated into an overall supervisory system that can include artificial intelligence, the system may not just control a measurement process for detecting cracks, but may also track over time the progression of those crack defects, estimate blade remaining life and notify operations personnel of blade conditions, oversee and report on component status and recommend best operating practices.

Unlike pyrometer systems that commonly use a single point of the desired surface to measure temperature, a system embodying aspects of the present invention would preferably use a focal plane array sensor (e.g., an array of charged coupled devices (CCD)) or imaging sensor to measure the emitted radiance of the entire area of the surface to be measured to obtain a real image of the individual blade, which can be analyzed using any suitable image evaluation/pattern recognition technique.

The term "radiance" is hereby defined as the total emittance, in this case, total thermal emittance, from the surface of an object. Emittance is synonymous with radiance, that is, radiant energy emitted by a free surface. Infrared is the region of the electromagnetic spectrum between microwave and visible light.

As will be appreciated by those skilled in the art, water vapor exhibits a relatively strong absorption band, such as in the range from approximately 6 μm to approximately 7 μm. Accordingly, the imaging sensor is configured to sense an infrared bandwidth selected to avoid such an absorption band. The infrared bandwidth is further selected to capture a sufficient amount of radiant energy in the steam turbine environment so that a plurality of thermal imaging points, as may be acquired by the imaging sensor, have sufficient resolution to identify a crack at an area of the blade prior to the crack growing to a critical length. In one exemplary embodiment, an infrared bandwidth suitable for meeting such objectives may be in the long field range of the infrared spectrum, such as ranging from approximately 8 μm to approximately 15 μm.

Figure 2:
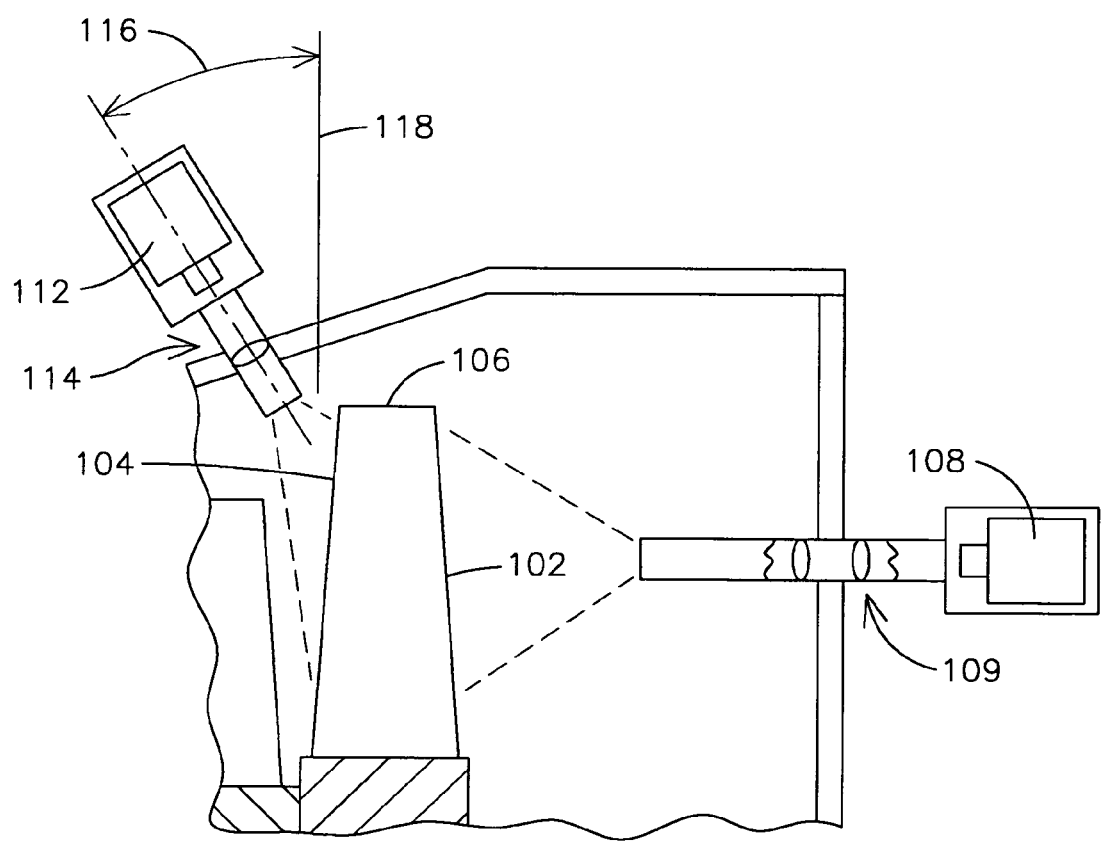
FIG. 2 illustrates a more detailed view of the blade monitor of FIG. 1

In one exemplary embodiment, as illustrated in FIG. 2, one can remotely monitor radiant energy from respective first and second areas 102 and 104 of a steam turbine blade 106 while the blade is rotating. In one example, the first area 102 may be part of suction side of the blade. In another example, the second area 104 may be part of a pressure side of the blade. It will be appreciated that the sectional blade profile illustrated in FIGS. 1 and 2, should be interpreted as a conceptual profile since the actual blade profile for a given turbine application may take any of various geometries as would be appreciated by one skilled in the art.

The monitoring of the first area may be performed with a first focal plane array imaging sensor 108 coupled to an optical system 109 (e.g., one or more lenses) disposed along an axis parallel (or nearly parallel) to an axis of rotation 110 (FIG. 1) of the blade to concurrently acquire a plurality of thermal imaging points spatially registered over the first area of the blade. The monitoring of the second area may be performed with a second focal plane array imaging sensor 112 coupled to an optical system 114 disposed at an angle 116 relative to an axis 118 disposed along a radial direction, perpendicular to the axis of rotation. To obtain an increased depth of field for this almost radial view (as determined by angle 116), the optical system may be arranged in accordance with the Scheimpflug principle. This arrangement can provide a plurality of thermal imaging points spatially registered over the second area of the blade having superior focusing over the entire radial length. As will be appreciated by those skilled in the art, the Scheimpflug principle provides guidance on how a plane of a sensing array should be tilted relative to the lens or lens system (optical axis) when focusing upon a plane that is not parallel to this plane of the sensing array (depth of field extension).

To evaluate individual blades, a controllable trigger mechanism, such as a triggering device 24 (FIG. 4) may be responsive to a spatial reference on the turbine shaft 25 to generate a measurement-triggering signal (e.g., once per rev signal) coupled to a data processor 30.

The first and second imaging sensors 108 and 112 are each respectively configured to sense an infrared bandwidth selected to avoid an absorption band of water vapor and are further selected to capture a sufficient amount of radiant energy in the steam turbine environment so that the plurality of thermal imaging points have sufficient resolution to identify a crack at any of such first and second areas of the blade prior to the crack growing to a critical length. In addition, given the relatively low-temperature environment in a steam turbine, the respective aperture stops provided by the lenses in optical systems 109 and 114 would be selected in a manner to sufficiently increase the amount of radiant energy collected by such optical systems to meet the foregoing objectives.

In one exemplary on-line embodiment, the blades are periodically thermally imaged, and differences of surface radiance are noted and tracked essentially in real-time operation of the individual blade. Additionally, rapid analysis and decision systems utilizing both expert and supervisory subsystems may be employed to summarize data and make decisions regarding the operation of the turbine. The expert systems would include blade life and crack growth algorithms that would forecast the operating time available once a crack is detected. The expert system would be interactive to allow the operator or a computer to change turbine operation conditions in virtual space and generate estimates of remaining life of the blade.

Figure 3:
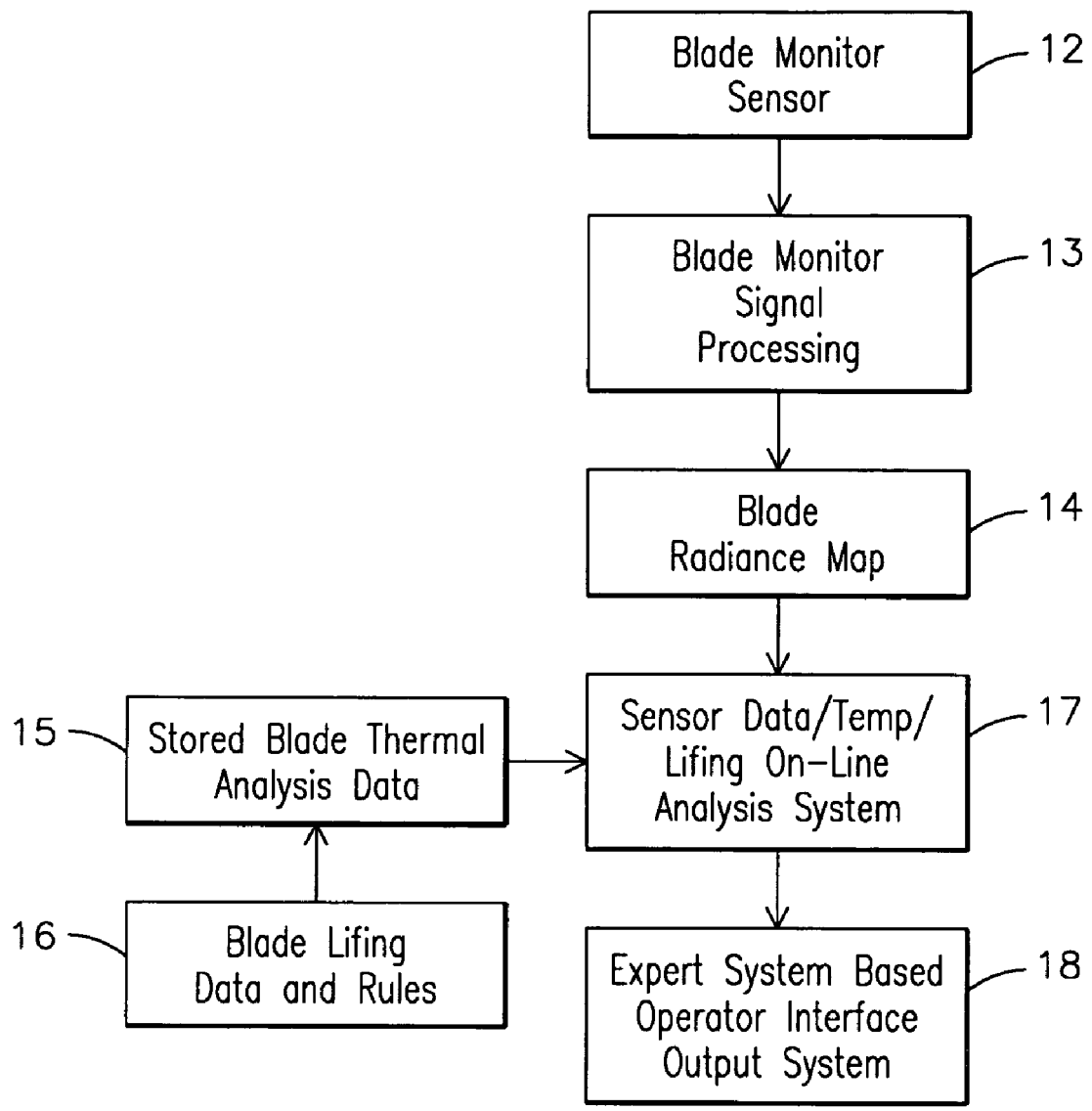
FIG. 3 is a block diagram of a flow of exemplary operational relationships as may be performed with a method embodying aspects of the present invention.

Aspects of this invention propose to address the development of an on-line blade monitor system for steam turbine by developing blade-monitoring systems and integrating them into a computerized high-speed analysis system that can be installed on an operating steam turbine. FIG. 3 depicts an exemplary proposed implementation of this concept. One may start with developing a clear understanding of the required system capabilities and a correlation with prospective sensor capabilities. The speed capabilities of sensor and computer analysis systems may also be evaluated. One exemplary embodiment is based upon a focal plane array that may monitor blades as they pass by a vantage viewing area.

The blade measuring/monitoring process may include a triggering step, such as may be performed with triggering device 24 (FIG. 4), a blade monitoring step, as may be performed with a blade monitor sensor 12, a signal processing step, such as may be performed with a signal processor 13, and a radiance mapping step 14, and may be based upon suitable modifications made to commercially available infrared imaging technology. This technology is able to acquire thermal images at sufficient speed and resolution to monitor high-speed events such as the motion of a turbine blade past a viewing port at linear speeds of approximately up to Mach 2. It is not necessary to view and acquire images of every blade every time it passes the camera, but it is necessary to acquire a single blade image over a short time interval. Preliminary calculations have shown that in order to obtain the resolution needed from a moving blade at Mach 2 speeds, the focal plane array camera should be able to integrate the IR signal within less than 1 microsecond. Otherwise, spatial distortions may render the image essentially useless. Data may be acquired for all blades and then correlated with previous images of each of the blades. Long term changes would be realized by comparison of current images with older archived images.

The sensor system is configured to provide useful data essentially in real time, and the analytical model is configured to predict component performance. One element of the computer system may be a storage and retrieval system that may compare on-line data for the assessment of the blade. Digital IR images for each blade in a row can be readily accessed and stored using frame grabbers and modern computer workstations. Also included may be a stored blade thermal analysis database 15, a blade life database 16, a sensor data/temperature/life on-line analysis system 17 and an expert system based operator interface output system 18. Thermal analysis database 15 may comprise up-to-date spatial data of radiance for each blade. Component life database 16 may comprise historical spatial data of radiance for each blade. Sensor/data/temperature/life on-line analysis system 17 may comprise a system that compares present data with historical data to look for evidence of blade failure. Expert system 18 may comprise a system that takes evidence of failure and tests against operating conditions, determines relevance, and estimates remaining life.

Figure 4:
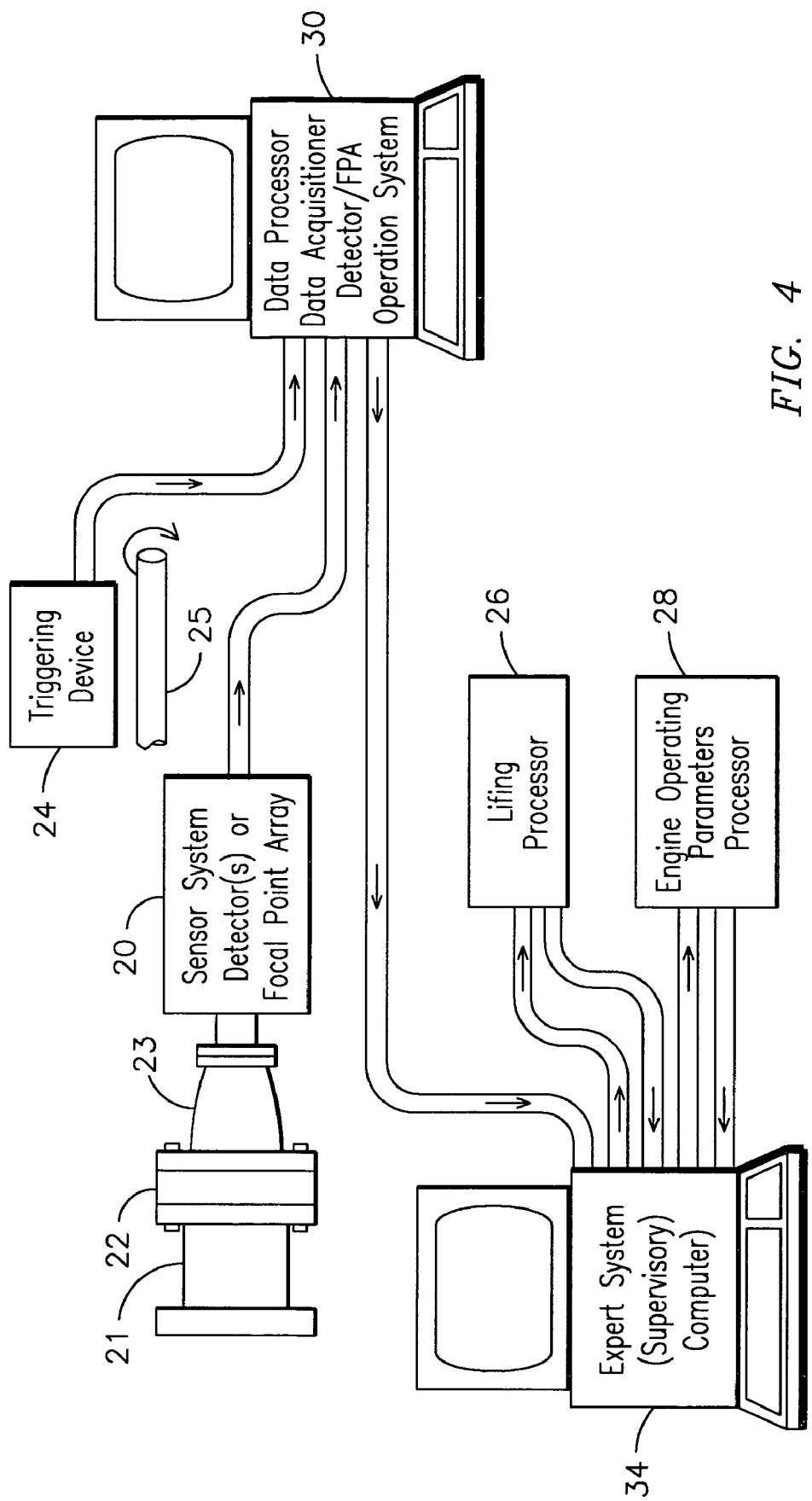
FIG. 4 is a schematic diagram of an exemplary blade monitor system embodying aspects of the present invention.

The computer analysis and operator interface may be a dual-level hierarchical system, as exemplarily shown in FIG. 4. At the lower level, a dedicated sensor computer 30 will monitor on-line sensor 20. Trigger device 24 may include an RPM sensor configured to, for example, generate a pulse per rev for triggering the individual measurements. The IR port 21 may provide a direct "line of sight" to the blade path. Pressure barrier 22 may allow IR signal through to sensor system 20. Optical system 23 may allow focal length adjustment for necessary magnification. Optical system 23 may further allow field of view adjustment as desired for any given application. For example, optical system 109 coupled to first focal plane array imaging sensor 108 (FIG. 2) may be configured to have a relatively wide field of view in order to image a relatively large surface area over the suction side of the blade. At the higher level, a supervisory computer 34 containing an advisory expert system may oversee the sensor computers 30. This supervisory system may contain knowledge that may identify an impending failure and prescribe corrective action. The supervisory computer may have at least two subsystems: a life processor 26 which determines remaining life of a blade, damage and an engine operating parameter processor 28 which continually monitors engine parameters like: temperature, speed, fuel consumption and power output.

The supervisory software 34 may store all the processed data coming from the blade through sensor 20 and the on-line temperature and life analysis systems. The data may be supplemented by common engine operating parameters.

Data may be processed into an appropriate format to demonstrate changes or excursions that require reporting to the control software. The control software may interpret the reported trends or excursions and notify or alert the operator of the finding. Different types of preprocessing logic may be used to identify excursions or trends. Raw data signals may be processed as collected. Some preprocessing steps may include a continually updated running average with statistical significance for ongoing data collection. This may establish a baseline for comparison of each refreshed data set. Excursions from this baseline may be brought to the attention and disposition of the expert system. Historical averages may be periodically stored for long-term trending and supervisory system disposition. The system may report information in the following categories: anomalies found on the image, remaining life of a blade, recommendations for optimizing specific operating parameters, and emergency alert. By continually monitoring the operating conditions, the remaining life for different future operating conditions may be forecasted. The operator may have the ability to balance power output and blade life depletion rate based on advice given by the control system software. This may optimize power output and outage scheduling for maximum operator control. The system may provide alarms for critical crack situations. The alarms may notify operators only in the event of eminent damage or failure. The system may also provide alarm signal outputs for connection to standard tripping control devices for the option of automatic tripping.

It will be appreciated that aspects of the present invention can also be embodied as computer readable code on a computer readable medium. The computer readable medium may be any data storage device that can store data, which thereafter can be read by a computer system. Examples of computer readable medium include read-only memory, random-access memory, CD-ROMs, DVDs, magnetic tape, optical data storage devices. The computer readable medium can also be distributed over network coupled computer systems so that the computer readable code is stored and executed in a distributed fashion.

Based on the foregoing specification, aspects of the present invention may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the invention. The computer readable media may be, for example, a fixed (hard) drive, diskette, optical disk, magnetic tape, semiconductor memory such as read-only memory (ROM), etc., or any transmitting/receiving medium such as the Internet or other communication network or link. The article of manufacture containing the computer code may be made and/or used by executing the code directly from one medium, by copying the code from one medium to another medium, or by transmitting the code over a network.

An apparatus for making, using or selling the invention may be one or more processing systems including, but not limited to, a central processing unit (CPU), memory, storage devices, communication links and devices, servers, I/O devices, or any sub-components of one or more processing systems, including software, firmware, hardware or any combination or subset thereof, which embody the invention as set forth in the claims.

User input may be received from the keyboard, mouse, pen, voice, touch screen, or any other means by which a human can input data to a computer, including through other programs such as application programs.

One skilled in the art of computer science will easily be able to combine the software created as described with appropriate general purpose or special purpose computer hardware to create a computer system or computer sub-system embodying aspects of the present invention.

The present invention may be embodied in other forms without departing from the spirit or essential attributes thereof, and accordingly, reference should be made to both the appended claims and the foregoing specification as indicating the scope of the invention.

We claim as our invention:

1. A method for inspecting a rotationally operating steam turbine blade, with the blade potentially undergoing degradation in a relatively low-temperature, and saturated steam environment found in the last blade rows of a low pressure stage steam turbine, the method comprising:

remotely monitoring radiant energy from respective first and second areas of the gas turbine blade while the blade is rotating, the monitoring of said first area being performed with a first focal plane array imaging sensor coupled to an optical system disposed along an axis generally parallel to an axis of rotation of the blade to concurrently acquire a plurality of thermal imaging points spatially registered over said first area of the blade, wherein said first area of the blade is part of a suction side of the blade, the monitoring of said second area being performed with a second focal plane array imaging sensor coupled to an optical system disposed at an angle relative to an axis along a radial direction to provide a view substantially along said radial direction, configuring said optical system to provide a sufficient depth of field along the view substantially along said radial direction to concurrently and within-focus acquire a plurality of thermal imaging points spatially registered over said second area of the blade, wherein said second area of the blade is part of a pressure side of the blade, wherein said first and second imaging sensors are each respectively configured to sense an infrared bandwidth selected to avoid an absorption band of water vapor and being further selected to capture a sufficient amount of radiant energy in said steam turbine environment so that said plurality of thermal imaging points have sufficient resolution to identify a crack at any of said first and second areas of the blade prior to said crack growing to a critical length;

processing said plurality of thermal imaging points to generate respective images of said first and second areas of the turbine blade to indicate the crack at any of said first and second areas of the turbine blade; and evaluating the crack indicated in any of the respective images, wherein said monitoring, processing and evaluating are effected within a sufficiently short period of time to avert growth of said crack to the critical length.

2. A system for inspecting a rotationally operating steam turbine blade, with the blade potentially undergoing degradation in a relatively low-temperature, and saturated steam environment of a steam turbine, the system comprising:

a monitor for remotely monitoring radiant energy from respective first and second areas of the gas turbine blade while the blade is rotating, said monitor comprising a measurement triggering device, a first focal plane array imaging sensor coupled to an optical system disposed along an axis substantially parallel to an axis of rotation of the blade to concurrently acquire a plurality of thermal imaging points spatially registered over said first area of the blade, wherein said first area of the blade is part of a suction side of the blade, said monitor further comprising a second focal plane array imaging sensor coupled to an optical system disposed at an angle relative to an axis along a radial direction to provide a view substantially along said radial direction, said optical system configured to provide a sufficient depth of field along the view substantially along the radial direction to concurrently and within-focus acquire a plurality of thermal imaging points spatially registered over said second area of the blade, wherein said second area of the blade is part of a pressure side of the blade, wherein said first and second imaging sensors are each respectively configured to sense an infrared bandwidth selected to avoid an absorption band of water vapor and being further selected to capture a sufficient amount of radiant energy in said steam turbine environment so that said plurality of thermal imaging points have sufficient resolution to identify a crack at any of said first and second areas of the blade prior to said crack growing to a critical length;

a processor configured to process said plurality of thermal imaging points to generate respective images of said first and second areas of the turbine blade to indicate the crack at any of said first and second areas of the turbine blade; and a module configured to evaluate the crack indicated in any of the respective images, wherein operations performed by said monitor, processor and evaluating module are effected within a sufficiently short period of time to avert growth of said crack to the critical length.

3. A method for inspecting a rotationally operating steam turbine blade, with the blade potentially undergoing degradation in a relatively low-temperature, and saturated steam environment of a steam turbine, the method comprising:

remotely monitoring radiant energy from an area of the gas turbine blade while the blade is rotating, said monitoring being performed with a focal plane array imaging sensor configured to concurrently acquire a plurality of thermal imaging points spatially registered over said area of the blade, said imaging sensor configured to sense an infrared bandwidth selected to avoid an absorption band of water vapor and being further selected to capture a sufficient amount of radiant energy in said steam turbine environment so that said plurality of thermal imaging points have sufficient resolution to identify a crack at the area of that blade prior to said crack growing to a critical length;

processing said plurality of thermal imaging points to generate an image of said area of the turbine blade to indicate the crack at the area of the turbine blade; and evaluating the crack indicated in the image, wherein said monitoring, processing and evaluating are effected within a sufficiently short period of time to avert growth of said crack to the critical length.

4. A system for inspecting a rotationally operating steam turbine blade, with the blade potentially undergoing degradation in a relatively low-temperature, and saturated steam environment of a steam turbine, the system, comprising:

a monitor configured to remotely monitor radiant energy from an area of the gas turbine blade while the blade is rotating, said monitor comprising a focal plane array imaging sensor configured to concurrently acquire a plurality of thermal imaging points spatially registered over said area of the blade, said imaging sensor configured to sense an infrared bandwidth selected to avoid an absorption band of water vapor and being further selected to capture a sufficient amount of radiant energy in said steam turbine environment so that said plurality of thermal imaging points have sufficient resolution to identify a crack at the area of that blade prior to said crack growing to a critical length;

a processor configured to process said plurality of thermal imaging points to generate an image of said area of the turbine blade to indicate the crack at the area of the turbine blade; and a module configured to evaluate the crack indicated in the image, wherein operation performed by said monitor, processor and evaluating module are effected within a sufficiently short period of time to avert growth of said crack to the critical length.

5. An article of manufacture comprising a computer program product comprising a computer-usable medium having a computer-readable code therein for inspecting a rotationally operating steam turbine blade, with the blade potentially undergoing degradation in a relatively low-temperature, and saturated steam environment found in the last blade rows of a low pressure stage steam turbine, the computer-readable code comprising:

computer-readable code for triggering a monitoring of radiant energy from respective first and second areas of the gas turbine blade while the blade is rotating, the monitoring of said first area being performed with a first focal plane array imaging sensor coupled to an optical system disposed along an axis generally parallel to an axis of rotation of the blade, and the monitoring of said second area being performed with a second focal plane array imaging sensor coupled to an optical system disposed at an angle relative to an axis along a radial direction to provide a view substantially along said radial direction;

computer-readable code for concurrently acquiring a plurality of thermal imaging points spatially registered over said first area of the blade, wherein said first area of the blade is part of a suction side of the blade;

computer-readable code for concurrently acquiring a plurality of thermal imaging points spatially registered over said second area of the blade, wherein said second area of the blade is part of a pressure side of the blade, wherein said first and second imaging sensors are each respectively configured to sense an infrared bandwidth selected to avoid an absorption band of water vapor and being further selected to capture a sufficient amount of radiant energy in said steam turbine environment so that said plurality of thermal imaging points have sufficient resolution to identify a crack at any of said first and second areas of the blade prior to said crack growing to a critical length;

computer-readable code for processing said plurality of thermal imaging points to generate respective images of said first and second areas of the turbine blade to indicate the crack at any of said first and second areas of the turbine blade; and computer-readable code for evaluating the crack indicated in any of the respective images, wherein said monitoring, processing and evaluating are effected within a sufficiently short period of time to avert growth of said crack to the critical length.

* * * * *